(12) United States Patent
Fokin et al.

(10) Patent No.: US 8,372,986 B2
(45) Date of Patent: Feb. 12, 2013

(54) RUTHENIUM-CATALYZED CYCLOADDITION OF ALKYNES AND ORGANIC AZIDES

(75) Inventors: Valery Fokin, Oceanside, CA (US); Guocheng Jia, Kowloon (HK); K. Barry Sharpless, La Jolla, CA (US)

(73) Assignees: The Scripps Research Institute, La Jolla, CA (US); The Hong Kong University of Science and Technology, Kowloon (HK)

( * ) Notice: Subject to any disclaimer, the term of this patent is extended or adjusted under 35 U.S.C. 154(b) by 684 days.

(21) Appl. No.: 11/992,696

(22) PCT Filed: Sep. 29, 2006

(86) PCT No.: PCT/US2006/038347
§ 371 (c)(1), (2), (4) Date: Jul. 19, 2010

(87) PCT Pub. No.: WO2007/041451
PCT Pub. Date: Apr. 12, 2007

(65) Prior Publication Data
US 2010/0286405 A1    Nov. 11, 2010

Related U.S. Application Data (60) Provisional application No. 60/722,488, filed on Sep. 30, 2005.

(51) Int. Cl.
*C07D 249/04* (2006.01)

(52) U.S. Cl. .................................................. 548/255

(58) Field of Classification Search ................ 548/255
See application file for complete search history.

(56) References Cited

FOREIGN PATENT DOCUMENTS
WO    WO 03/101972 A1 * 12/2003

\* cited by examiner

*Primary Examiner* — Joseph Kosack
(74) *Attorney, Agent, or Firm* — Olson & Cepuritis, Ltd.

(57) ABSTRACT

A convenient process for the regioselective synthesis of 1,5-disubstituted 1,2,3-triazoles and 1,4,5-trisubstituted 1,2,3-triazoles from organic azides and alkynes employs catalytic ruthenium.

30 Claims, 5 Drawing Sheets

Figure 1

| Entry | Product | | Reaction time, h | yield, % |
|---|---|---|---|---|
| 1 |  | 1a | 2 | 80 |
| 2 |  | 2a | 4 | 93 |
| 3 |  | 3a | 3 | 82 |
| 4 |  | 4a | 4 | 82 |
| 5 |  | 5a | 2 | 81 |
| 6 |  | 6a | 2.5 | 94 |
| 7 |  | 7a | 4 | 87 |
| 8 |  | 8a | 2 (THF, 60 °C) | 89 |
| 9 |  | 9a | 2 (THF, 60 °C) | 82 |
| 10 |  | 10a | 12 (THF, 60 °C) | 54 |
| 11 |  | 11a | 6 (THF, 60 °C) | 32 |

RUTHENIUM-CATALYZED CYCLOADDITION OF ALKYNES AND ORGANIC AZIDES

This application is the national stage of International Application Ser. No. PCT/US2006/038347, filed on Sep. 29, 2006, which claims the benefit of U.S. Provisional Application Serial No. 60/722,488, filed on Sep. 30, 2005, the disclosures of which are incorporated herein by reference.

STATEMENT OF GOVERNMENT SUPPORT

This invention was made with government support under contract number GM 028384 awarded by the National Institutes of Health. The government has certain rights in the invention.

FIELD OF INVENTION

The invention relates to synthetic processes for making 1,2,3-triazoles. More particularly, the invention relates to the use of ruthenium for catalyzing a cycloaddition of alkynes and organic azides for synthesizing 1,5-disubstituted 1,2,3-triazoles and 1,4,5-trisubstituted 1,2,3-triazoles.

BACKGROUND

Huisgen's dipolar cycloaddition of organic azides and alkynes is the most direct route to 1,2,3-triazoles (Huisgen, R. In 1,3-*Dipolar Cycloaddition Chemistry*; Padwa, A. Ed.; Wiley: New York, 1984). However, because of the high activation energy (ca 24-26 kcal/mol), these cycloadditions are very slow even at elevated temperature and prolonged heating (80-120° C. for 12-24 hours), forming mixtures of regioisomers. The discovery that Cu(I) efficiently and regiospecifically catalyzes cycloadditions of terminal alkynes and azides, providing 1,4-disubstituted 1,2,3-triazoles under mild conditions, was a welcome advance (Rostovtsev, V. V.; et al. *Angew. Chem. Int. Ed.* 2002, 41, 2596; Tornoe, C. W.; et al. *J. Org. Chem.* 2002, 67, 3057). The Cu(I)-catalyzed azide-alkyne cycloaddition (CuAAC), perhaps the most powerful click reaction (Kolb, H. C.; Sharpless, K. B. *Drug Discovery Today*, 2003, 8, 1128) to date, has quickly found many applications in chemistry, biology and materials science (Home, W. S.; et al. *J. Am. Chem. Soc.* 2004, 126, 15366; Manetsch, R.; et al. *J. Am. Chem. Soc.* 2004, 126, 12809; Link, A. J.; et al. *J. Am. Chem. Soc.* 2004, 126, 10598; Zhou, Z.; Fahrni, C. J. *J. Am. Chem. Soc.* 2004, 126, 8862; Lewis, W. G.; et al. *J. Am. Chem. Soc.* 2004, 126, 9152; Wu, P.; Feldman, A. K.; et al. *Angew. Chem., Int. Ed.* 2004, 43, 3928; Meng, J. C.; et al. *Angew. Chem. Int. Ed.* 2004, 43, 1255; Opsteen, J. A.; van Hest, J. C. M. *Chem. Commun.* 2005, 57; Punna, S.; et al. *Angew. Chem. Int. Ed.* 2005, 44, 2215).

CuAAC does not afford selective access to the complimentary regioisomers of 1,4-disubstituted 1,2,3-triazoles. Although 1,5-disubstituted triazoles and 1,4,5-trisubstituted triazoles can be synthesized by the reaction of bromomagnesium acetylides with organic azides (Krasinski, A.; Fokin, V. V.; Sharpless, K. B. *Org. Lett.* 2004, 6, 1237), this method lacks the scope and convenience of the CuAAC process. What is needed is a process for synthesizing 1,5-disubstituted triazoles and 1,4,5-trisubstituted triazoles by a ruthenium-catalyzed "fusion" of organic azides with alkynes.

Catalytic transformations of alkynes mediated by ruthenium complexes are well known, and evidence for the intermediacy of ruthenium (II) acetylide, vinylidene and ruthenametallacyclic complexes has been provided (Naota, T.; et al. *Chem. Rev.* 1998, 98, 2599; Bruneau, C.; Dixneuf, P. H. *Acc. Chem. Res.* 1999, 32, 311; Trost, B. M.; et al. *Chem. Rev.* 2001, 101, 2067). What is needed is ruthenium complexes employable in azide-alkyne cycloaddition reactions.

SUMMARY

A convenient catalytic process using ruthenium for the regioselective synthesis of 1,5-disubstituted 1,2,3-triazoles and 1,4,5-trisubstituted 1,2,3-triazoles from organic azides and alkynes is disclosed herein. The catalytic process is not limited to terminal alkynes. Together with the Cu-AAC, these transformations allow selective preparation of both regioisomers of 1,2,3-triazoles, heterocycles that have recently become popular as a means for establishing reliable and stable connections in organic synthesis, medicinal chemistry, and materials science.

One aspect of the invention is directed to a process for the formation of a 1,5-disubstituted 1,2,3-triazole or a 1,4,5-trisubstituted 1,2,3-triazole. In the first step of the process, a first compound having an acetylene group is admixed with a second compound having an azide group in a solvent for forming a reaction mixture. In a preferred mode of the first step, the first and second compounds are admixed in equal equivalents. In another preferred mode of the first step, the first compound is admixed in slight excess with the second compound. In another preferred mode of the first step, the concentration of the first and second compounds is between 0.01 and 1 M. In another preferred mode of the first step, the concentration of the first and second compounds is between 0.07-0.15 M. In another preferred mode of the first step, the solvent is selected from the group consisting of: benzene, toluene, THF, and dioxane. Then, in the second step of the process, the reaction mixture of the first step is contacted with a quantity of ruthenium catalyst sufficient for catalyzing the formation of the 1,5-disubstituted 1,2,3-triazole or the 1,4,5-trisubstituted 1,2,3-triazole. In a preferred mode, the ruthenium catalyst includes one or more ligands. Preferred ruthenium catalysts are selected from the group consisting of Cp*RuCl(PPh$_3$)$_2$, [Cp*RuCl$_2$]$_2$, Cp*RuCl(NBD), and Cp*RuCl(COD). Pentamethylcyclopentadienyl anion is a preferred ligand. In another preferred mode of the second step, the minimum concentration of ruthenium catalyst is between 1 and 5 mol %. In another preferred mode of the second step, the reaction mixture is stirred for a time sufficient for the azide compound to react completely. In another preferred mode of the second step, the temperature of the reaction is between room temperature and reflux temperature. In another preferred mode of the second step, the reaction mixture is stirred with external heating sufficient to cause refluxing of the solution. Optionally, the process may also include a third step wherein, the 1,5-disubstituted 1,2,3-triazole or 1,4,5-trisubstituted 1,2,3-triazole formed in the second step is separated from the reaction mixture.

Another aspect of the invention is directed to a chemical complex represented by the following structure:

(Formula I)

In Formula I, $R_1$ is selected from the group of radicals consisting of alkyl, alkenyl, aryl, heteroaryl, benzyl, propargyl, cycloalkyl, trialkylsilyl, alkyldiarylsilyl, dialkylarylsilyl, trialkylstannyl, triarylsilyl, and cycloalkenyl; $R_2$ is selected from the group of radicals consisting of alkyl, alkenyl, aryl, heteroaryl, benzyl, cycloalkyl, trialkylsilyl, alkyldiarylsilyl, dialkylarylsilyl, trialkylstannyl, triarylsilyl, and cycloalkenyl; $R_3$ is selected from the group of radicals consisting of hydrogen, alkyl, alkenyl, aryl, heteroaryl, benzyl, propargyl, cycloalkyl, trialkylsilyl, alkyldiarylsilyl, dialkylarylsilyl, trialkylstannyl, triarylsilyl, and cycloalkenyl; and X is selected from the group of radicals consisting of halide, alkylsulfonate, arylsulfonate and cyanide. In a preferred embodiment of Formula I, X is chloride. In another preferred embodiment of Formula I, $R_3$ is hydrogen.

Another aspect of the invention is directed to a chemical complex represented by the following structure:

(Formula II)

In Formula II, $R_1$ is selected from the group of radicals consisting of alkyl, alkenyl, aryl, heteroaryl, benzyl, propargyl, cycloalkyl, trialkylsilyl, alkyldiarylsilyl, dialkylarylsilyl, trialkylstannyl, triarylsilyl, and cycloalkenyl; $R_2$ is selected from the group of radicals consisting of alkyl, alkenyl, aryl, heteroaryl, benzyl, cycloalkyl, trialkylsilyl, alkyldiarylsilyl, dialkylarylsilyl, trialkylstannyl, triarylsilyl, and cycloalkenyl; $R_3$ is selected from the group of radicals consisting of hydrogen, alkyl, alkenyl, aryl, heteroaryl, benzyl, propargyl, cycloalkyl, trialkylsilyl, alkyldiarylsilyl, dialkylarylsilyl, trialkylstannyl, triarylsilyl, and cycloalkenyl; and X is selected from the group of radicals consisting of halide, alkylsulfonate, arylsulfonate and cyanide. In a preferred embodiment of Formula II, X is chloride. In another preferred embodiment of Formula II, $R_3$ is hydrogen.

DETAILED DESCRIPTION

The reaction of benzyl azide with phenylacetylene in the presence of various ruthenium complexes is characterized herein. In these screens, a mixture of benzyl azide and phenylacetylene (1:1.5 equiv., respectively) in benzene was heated at 80° C. for 4 hours in the presence of 5% mol of a ruthenium complex. Analysis of the resulting reaction mixture was done by $^1$H NMR. As revealed in FIG. 1, Ru(II) complexes do indeed catalyze the formation of 1,2,3-triazoles, with catalytic activity and regioselectivity observed being a sensitive function of the ligand environment around the ruthenium catalytic center.

Thus, in the presence of the acetate complex, $Ru(OAc)_2(PPh_3)_2$, the azide was completely consumed, and the 1,4-disubstituted triazole product 1b, together with small amounts of dimers and oligomers of phenylacetylene, was formed.

Complexes such as $RuCl_2(PPh_3)_3$ and $RuHCl(CO)(PPh_3)_3$ were rather ineffective: in their presence, less than 20% of benzyl azide reacted with phenylacetylene to give 1,4-disubstituted triazole 1b.

In contrast, $CpRuCl(PPh_3)_2$ catalyst resulted in 50% conversion of the reactants to a mixture of 1,5- and 1,4-disubstituted triazoles 1a and 1b in ca. 5.8:1 ratio. Then, a simple switch to the pentamethyl analog, $Cp*RuCl(PPh_3)_2$, effected formation of only 1,5-regioisomer 1a, with complete conversion. Reactions with other [Cp*Ru] complexes such as $[Cp*RuCl_2]_2$, $Cp*RuCl(NBD)$, and $Cp*RuCl(COD)$ gave results similar to that with $Cp*RuCl(PPh_3)_2$. This [Cp*RuCl]-based regiocontrol is useful because no accounts reporting catalytic synthesis of 1,5-disubstituted triazoles from terminal alkynes and azides have been published (Mocharla, V. P.; et al. Angew. Chem. Int. Ed. 2005, 44, 116; Dondoni, A.; et al. Org. Lett. 2004, 6, 2929; Wroblewski, A. E.; Glowacka, I. E. Tetrahedron Asymmetry, 2004, 15, 1457; Liu, J.; et al. J. Org. Chem. 2004, 69, 6273).

To evaluate the scope of this new ruthenium-catalyzed process with respect to the alkyne component, reactions of benzyl azide with several terminal alkynes were carried out. Likewise, reactivity of representative azides with phenylacetylene was studied. Typically, the reactions were performed with 1 mol % of $Cp*RuCl(PPh_3)_2$ catalyst at 0.07-0.15 M concentration of the components in refluxing benzene. Complete consumption of the benzyl azide at the end of the reaction was confirmed by $^1$H NMR analysis of the final reaction mixture. The results are easy to appreciate through the examples presented in FIG. 2. Thus, both aromatic and aliphatic alkynes reacted with benzyl azide to give the corresponding 1,5-disubstituted 1,2,3-triazoles. Alkynes with hydroxyl and aldehyde functional groups (entries 5,6, and 7) also readily participated in the reaction. Similarly, variations in the steric environment around the alkyne, at least to the extent represented by the cases herein, had no effect on the regioselectivity of the process.

In contrast, the nature of the azide component appears to have a considerable effect on the outcome of the reaction, both in terms of regioselectivity and catalytic efficiency.

Although 1,5-triazole products were obtained in excellent yields from primary aliphatic azides, such as phenethyl azide (entry 8) and ω-azidobutanol (entry 9), tertiary azides, such as tert-butyl and 1-adamantyl azide (entry 10) produced triazoles in only modest yields after 6 hours. However, higher catalyst loading (5 mol %) and extended reaction time resulted in improved yields. And finally, it was shown that reactions of aryl azides (entry 11) were poor across the board. They were hampered by low conversions and formation of noticeable amount of byproducts, especially when more forcing conditions were tried.

A brief examination of the effect of the solvent, temperature and concentration of reactants revealed that benzene, toluene, THF, and dioxane perform equally well. Protic solvents had a detrimental effect on both yield and regioselectivity. Thus, benzyl azide reacted with phenylacetylene significantly slower in refluxing isopropanol (5 h, 2 mol % of Cp*RuCl(PPh$_3$)$_2$, 70% conversion), and a mixture of regioisomeric products 1a and 1b (7:1) was formed. In most cases, concentration of the azide and alkyne can be varied from 0.01 to 1 M without a noticeable effect on conversion and regioselectivity. Likewise, reactions can be carried out at temperatures ranging from RT to 80° C. For example, benzyl azide was almost quantitatively converted to the corresponding triazoles when it was allowed to react with a slight excess of Ph$_2$C(OH)C≡CH or PhC≡CH in benzene at RT for 24 hours in the presence of 5% mol Cp*RuCl(PPh$_3$)$_2$.

The structures of new triazoles are fully consistent with their $^1$H, $^{13}$C NMR and MS data (See Supporting Information for the details). In addition, the solid-state structures of 1a, 6a and 7a have also been confirmed by X-ray diffraction studies.

Figure 3:
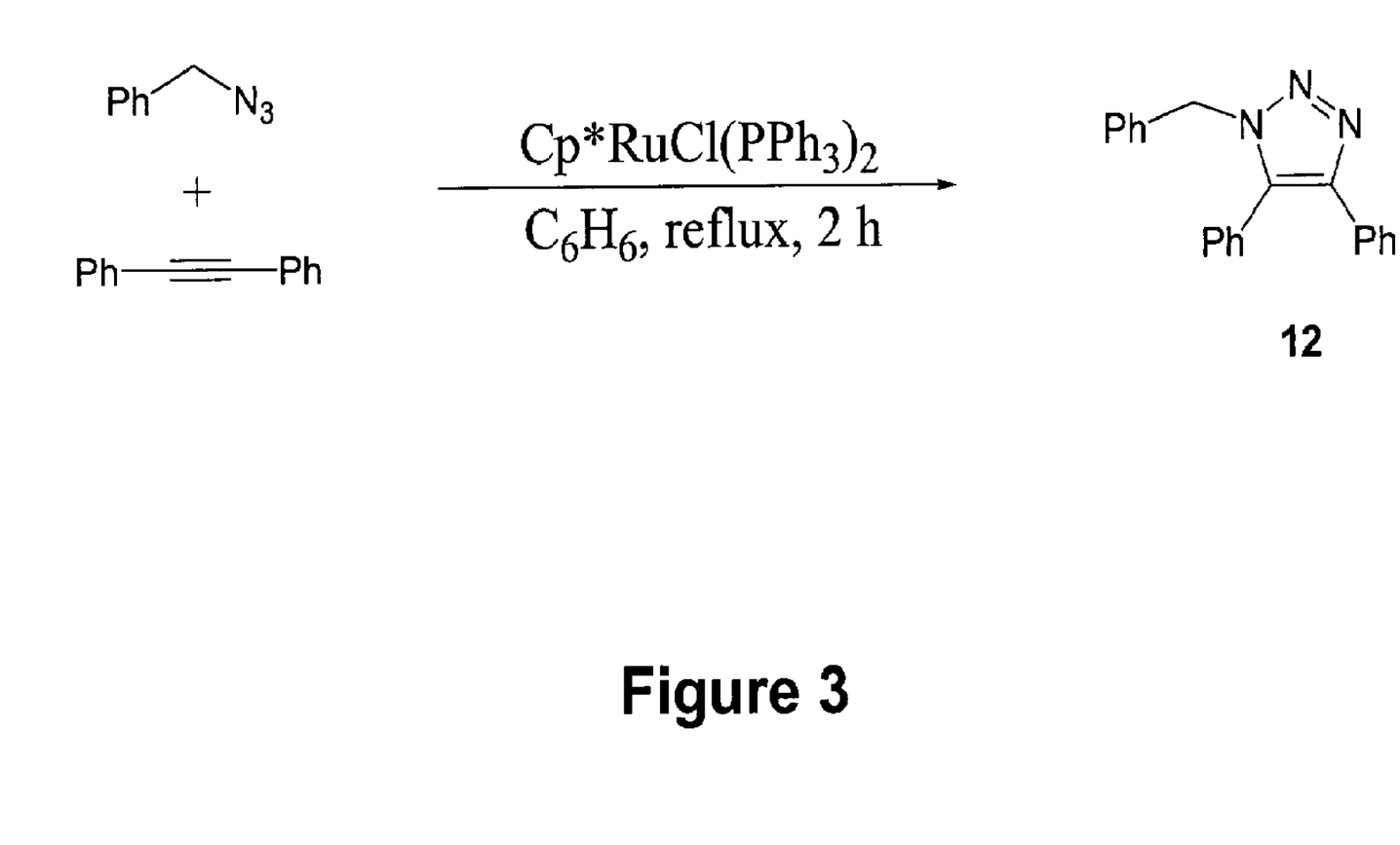
FIG. 3 illustrates a reaction with internal acetylenes are possible with these conditions giving rise to 1,4,5-trisubstituted 1,2,3-triazoles.

Since Cu(I) acetylides seem to be the bona fide intermediates in the CuAAC (Himo, F.; et al. *J. Am. Chem. Soc.* 2005, 127, 210; Rodionov, V. O.; et al. *Angew. Chem. Int. Ed.* 2005, 44, 2210), this transformation is limited to terminal alkynes. The Cp*Ru system, in fortunate contrast, is active with internal alkynes as well. For example, when a mixture of diphenylacetylene and benzyl azide (1:1.1 equiv., 0.15 M) was refluxed in benzene in the presence of ca. 1% mol of Cp*RuCl (PPh$_3$)$_2$ for 2 hours, the benzyl azide was completely converted to the triazole 12 (FIG. 3). The uncatalyzed reaction was very sluggish, and only a trace amount of triazole was detected even after 24 hours at reflux.

Since both terminal and internal alkynes participate in catalysis, the involvement of ruthenium acetylides is unlikely (and not even possible for the latter). Of course, cyclotrimerization of alkynes is well known and, for the specific case of the Cp*RuCl(COD), has been shown to proceed via ruthenacyclopentadienesi (Kirchner, K.; et al. *J. Am. Chem. Soc.* 2003, 125, 11721; Yamamoto, Y.; et al. *J. Am. Chem. Soc.* 2003, 125, 12413). Therefore, it is disclosed herein that the newly-discovered Ru-catalyzed triazole annulations represent a simple, and early, shunt off the usual alkyne oligomerization sequence. That is, oxidative coupling of an alkyne and an azide on ruthenium initially gives a six-membered ruthenacycle (FIG. 4; A is more likely than B), which then undergoes reductive elimination releasing the aromatic triazole product.

Experimental Procedures

All manipulations were carried out under a nitrogen atmosphere using standard Schlenk techniques, unless otherwise stated. $^1$H and $^{13}$C NMR chemical shifts are relative to TMS. Mass Spectra were collected on a Finnigan TSQ 7000 Spectrometer.

General Procedure for Cp*RuCl(PPh$_3$)$_2$ Catalyzed Cycloadditions.

A mixture of azide, alkyne and Cp*RuCl(PPh$_3$)$_2$ in an organic solvent (20 mL) was stirred (either at reflux or room temperature) for a given period of time. The progress of the reaction was monitored by $^1$H NMR or GC. In most of the reactions, the benzyl azide was consumed completely at the end of the reaction. The solvent was removed under vacuum and the product was purified by silica gel chromatography. The unreacted phenylacetylene and traces of side products were first eluted out with hexane, followed by 1/1 hexane/ether. The pure 1,5-disubstituted triazole or 1,4,5-trisubstituted 1,2,3-triazole product was then obtained by elution with ether or chloroform.

1-benzyl-5-phenyl-1H-1,2,3-triazole (1a)

Benzyl azide (0.400 g, 3.00 mmol), phenylacetylene (0.500 mL, 4.55 mmol), Cp*RuCl(PPh$_3$)$_2$ (25 mg, 0.031 mmol). Solvent, benzene; reaction temperature, 80° C., reaction time, 2 hours; yield, 0.56 g (80%).

Benzyl azide (0.200 g, 1.50 mmol), phenylacetylene (0.300 mL, 2.73 mmol), Cp*RuCl(PPh$_3$)$_2$ (25 mg, 0.031 mmol). Solvent, tetrahydrofuran; reaction temperature, 65° C.; reaction time, 3 hours; yield, 0.26 g (74%).

Benzyl azide (0.100 g, 0.751 mmol), phenylacetylene (0.150 mL, 1.37 mmol), Cp*RuCl(PPh$_3$)$_2$ (30 mg, 0.038 mmol). Solvent, benzene; reaction temperature, r.t.; reaction time, 24 hours; yield, 0.13 g (75%). EI-MS: m/z 236 [M+1].

1-benzyl-5-(2-naphthyl)-1H-1,2,3-triazole (2a)

Benzyl azide (0.400 g, 3.00 mmol), 2-ethynylnaphthalene (0.503 g, 3.31 mmol), Cp*RuCl(PPh$_3$)$_2$ (25 mg, 0.031 mmol). Solvent, benzene; reaction temperature, 80° C.; reaction time, 4 hours; yield, 0.80 g (93%). EI-MS: m/z 285 [M$^{+1}$.

1-benzyl-5-butyl-1H-1,2,3-triazole (3a)

Benzyl azide (0.340 g, 2.55 mmol), 1-hexyne (0.580 ml, 5.05 mmol), Cp*RuCl(PPh$_3$)$_2$ (50 mg, 0.063 mmol). Solvent, benzene; reaction temperature, 80° C.; reaction time, 3 hours; yield, 0.45 g (82%). EI-MS: m/z 216 [M+1].

1-benzyl-5-(tert-butyl)-1H-1,2,3-triazole (4a)

Benzyl azide (0.400 g, 3.00 mmol), 3,3-dimethyl-1-butyne (0.556 ml, 4.51 mmol), Cp*RuCl(PPh$_3$)$_2$ (50 mg, 0.063 mmol). Solvent, benzene; reaction temperature, 80° C.; reaction time, 4 hours; yield, 0.54 g (83%). EI-MS: m/z 216 [M+1].

4-(1-benzyl-1H-1,2,3-triazol-5-yl)benzaldehyde (5a)

Benzyl azide (0.200 g, 1.50 mmol), 4-ethynylbenzaldehyde (0.200 g, 1.54 mmol), Cp*RuCl(PPh$_3$)$_2$ (25 mg, 0.031 mmol). Solvent, benzene; reaction temperature, 80° C.; reaction time, 2 hours; yield, 0.32 g (81%). EI-MS: m/z 264 [M+1].

2-(1-benzyl-1H-1,2,3-triazol-5-yl)propan-2-ol (6a)

Benzyl azide (0.400 g, 3.00 mmol), 2-methyl-3-butyn-2-ol (0.290 ml, 3.00 mmol), Cp*RuCl(PPh$_3$)$_2$ (25 mg, 0.031 mmol). Solvent, benzene; reaction temperature, 80° C.; reaction time, 2.5 hours; yield, 0.63 g (96%). EI-MS: m/z 218 [M+1].

(1-benzyl-1H-1,2,3-triazol-5-yl)diphenylmethanol (7a)

Benzyl azide (0.400 g, 3.00 mmol), 1,1-diphenyl-2-propyn-1-ol (0.688 g, 3.31 mmol), Cp*RuCl(PPh$_3$)$_2$ (25 mg, 0.031 mmol). Solvent, benzene; reaction temperature, 80° C.; reaction time, 4 hours; yield, 0.89 g (87%).

Benzyl azide (0.200 g, 1.50 mmol), 1,1-diphenyl-2-propyn-1-ol (0.344 g, 1.65 mmol), Cp*RuCl(PPh$_3$)$_2$ (60 mg, 0.75 mmol). Solvent, benzene; reaction temperature, r.t.; reaction time, 24 hours; yield, 0.43 g (83%).

Benzyl azide (0.200 g, 1.50 mmol), 1,1-diphenyl-2-propyn-1-ol (0.344 g, 1.65 mmol), Cp*RuCl(PPh$_3$)$_2$ (12 mg, 0.015 mmol). Solvent, benzene; reaction temperature, 80° C.;

reaction time, 4 hours; yield, 0.39 g (75%). The reaction was performed under air. EI-MS: m/z 342 [M+1].

1-phenethyl-5-phenyl-1H-1,2,3-triazole (8a)

Phenethyl azide (148 mg, 1 mmol), phenylacetylene (113 mg, 1.1 mmol), Cp*RuCl(PPh$_3$)$_2$ (8 mg, 0.01 mmol, 1 mol %). Solvent: THF, 10 mL, 60° C., 2 hours. Off-white product obtained in 89% yield (221 mg). ESI-MS: m/z 250, [M+H].

3-(5-phenyl-1H-1,2,3-triazol-1-yl)propan-1-ol (9a)

3-Azidopropanol (101 mg, 1 mmol), phenylacetylene (113 mg, 1.1 mmol), Cp*RuCl(PPh$_3$)$_2$ (8 mg, 0.01 mmol, 1 mol %). Solvent: THF, 10 mL, 60° C., 2 hours. White microcrystalline product was obtained in 82% yield (167 mg). ESI-MS: m/z 204, [M+H].

1-adamantyl-5-phenyl-1H-1,2,3-triazole (10a)

1-Azidoadamantane (177 mg, 1 mmol), phenylacetylene (113 mg, 1.1 mmol), Cp*RuCl(PPh$_3$)$_2$ (8 mg, 0.01 mmol, 1 mol %). Solvent: THF, 10 mL, 60° C., 12 hours. Product obtained as off-white powder in 52% yield (145 mg). ESI-MS: m/z 280, [M+H].

1-tolyl-5-phenyl-1H-1,2,3-triazole (11a)

4-Tolyl azide (133 mg, 1 mmol), phenylacetylene (113 mg, 1.1 mmol), Cp*RuCl(PPh$_3$)$_2$ (16 mg, 0.02 mmol, 2 mol %). Solvent: THF, 10 mL, 60° C., 6 hours. Slightly yellow product obtained in 51% yield (120 mg). ESI-MS: m/z 236, [M+H].

1-benzyl-4,5-diphenyl-1H-1,2,3-triazole (12)

Benzyl azide (0.400 g, 3.00 mmol), diphenylacetylene (0.588 g, 3.30 mmol), Cp*RuCl(PPh$_3$)$_2$ (25 mg, 0.031 mmol). Solvent, benzene; reaction temperature, 80° C.; reaction time, 2 hours; yield, 0.75 g (80%). EI-MS: m/z 312 [M+1].

Ru(OAc)$_2$(PPh$_3$)$_2$ catalyzed reactions.

A mixture of azide, phenylacetylene and Ru(OAc)$_2$(PPh$_3$)$_2$ was refluxed in 20 mL of benzene for 4 hours. The progress of the reaction was monitored by $^1$H NMR. The azide was consumed completely at the end of the reaction, as confirmed by NMR. The solvent was removed under reduced pressure and the product was purified by silica gel column chromatography. The unreacted phenylacetylene and the side products were first eluted out with hexane, and 2/1 hexane/ether. The pure 1,4-substituted triazole was then obtained by elution with 1/1 hexane/ether.

CpRu(PPh$_3$)$_2$Cl catalyzed reactions.

A mixture of benzyl azide (0.200 g, 1.50 mmol), phenylacetylene (0.250 mL, 2.25 mmol) and CpRu(PPh$_3$)$_2$Cl (54.54 mg, 0.0751 mmol) was refluxed in 20 mL of benzene for 8 hours. The progress of the reaction was monitored by $^1$H NMR. The azide was consumed completely at the end of the reaction, as confirmed by NMR. The solvent was removed under vacuum and the product was purified by silica gel column chromatography. The unreacted phenylacetylene and the side products were first eluted out with hexane, and 2/1 hexane/ether. The 1:5.8 mixed 1,4-/1,5-disubstituted triazoles were then obtained by elution with 1/1 hexane/ether.

DETAILED DESCRIPTION OF FIGURES

Figure 1:
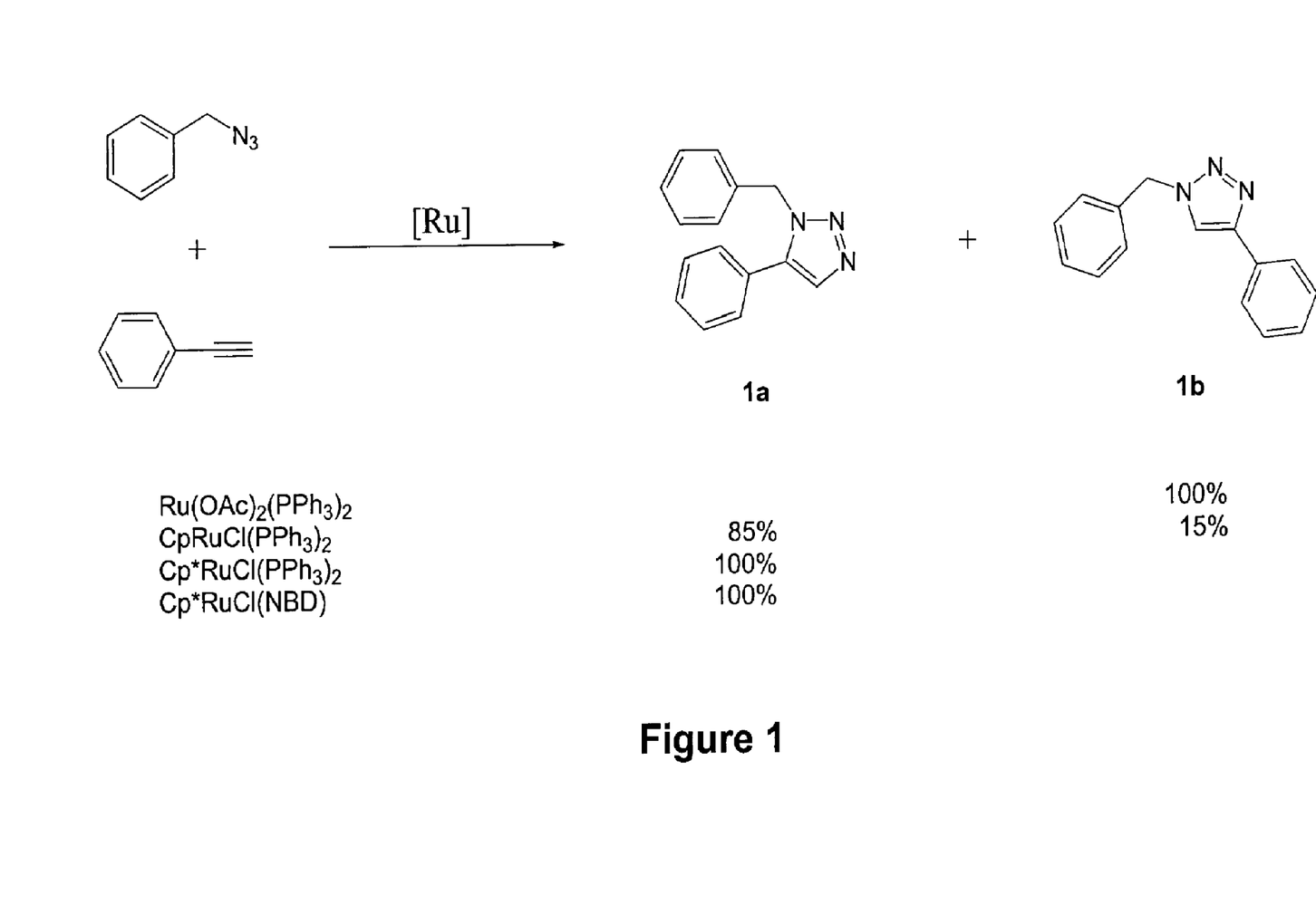
FIG. 1 illustrates a Ru-catalyzed cycloaddition of benzyl azide and phenylacetylene and the regioisomer ratios obtained from different catalysts.

FIG. 1 shows the Ru-catalyzed cycloaddition of benzyl azide and phenylacetylene and the regioisomer ratios obtained from different catalysts. The catalysts were screened under the following conditions, 5 mol % ruthenium complex, benzyl azide (1.0 equivalents), phenylacetylene (1.5 equivalents), benzene, reflux, 4 hours. The catalytic activity and regioselectivity observed are a sensitive function of the ligand environment around the ruthenium center. Thus, in the presence of the acetate complex, Ru(OAc)$_2$(PPh$_3$)$_2$, the azide was completely consumed, and the 1,4-disubstituted triazole product 1b, together with small amounts of dimers and oligomers of phenylacetylene, was formed. Complexes such as RuCl$_2$(PPh$_3$)$_3$ and RuHCl(CO)(PPh$_3$)$_3$ were rather ineffective: in their presence, less than 20% of benzylazide reacted with phenylacetylene to give 1,4-disubstituted triazole 1b. In contrast, CpRuCl(PPh$_3$)$_2$ catalyst resulted in 50% conversion of the reactants to a mixture of 1,5- and 1,4-disubstituted triazoles 1a and 1b in ca. 5.8:1 ratio. Then, a simple switch to the pentamethyl analog, Cp*RuCl(PPh$_3$)$_2$, effected formation of only 1,5-regioisomer 1a, with complete conversion. Reactions with other [Cp*Ru] complexes such as [Cp*RuCl$_2$]$_2$, Cp*RuCl(NBD), and Cp*RuCl(COD) gave results similar to that with Cp*RuCl(PPh$_3$)$_2$.

Figure 2:
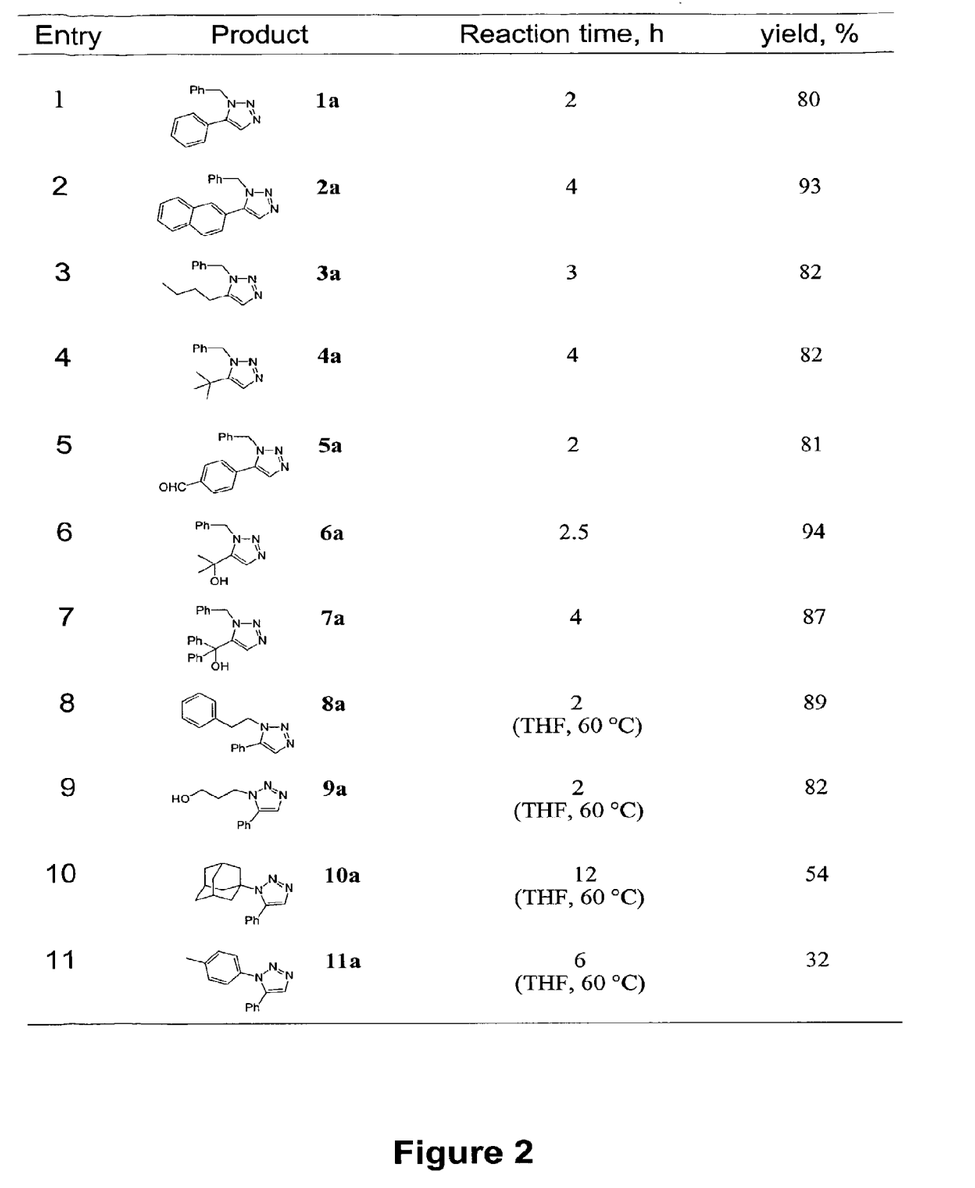
FIG. 2 illustrates a table showing the scope of the reaction with various azides and alkynes.

FIG. 2 is a table showing the scope of the reaction with various azides and alkynes. The reaction was carried out on a 1-3 mmol scale at 80° C. with 1-2.5 mol % of Cp*RuCl(PPh$_3$)$_2$ in benzene solvent unless noted otherwise in the table. The concentration of components in refluxing benzene was between 0.07-0.15 M. The aromatic and aliphatic alkynes reacted well with the benzyl azide substrate giving yields in the 81-94% range. The presence of hydroxyl and aldehyde groups on the alkyne did not affect the reaction. The groups on the azide had a strong effect on the efficiency of the reaction. The tertiary azide, adamantyl azide reacted only sluggishly with phenylacetylene as seen by the long reaction time and low yield. The aryl azide gave only a poor yield. Reaction with the aryl azides showed low conversions and formation of noticeable amounts of byproducts, especially when more forcing conditions were tried.

FIG. 3 shows a reaction with internal acetylenes are possible with these conditions. A mixture of diphenylacetylene and benzyl azide (1:1.1 equivalent, 0.15 M) was refluxed in benzene in the presence of 1 mol % of Cp*RuCl(PPh$_3$)$_2$ for 2 hours and the benzyl azide was completely converted to the triazole 12.

Figure 4:
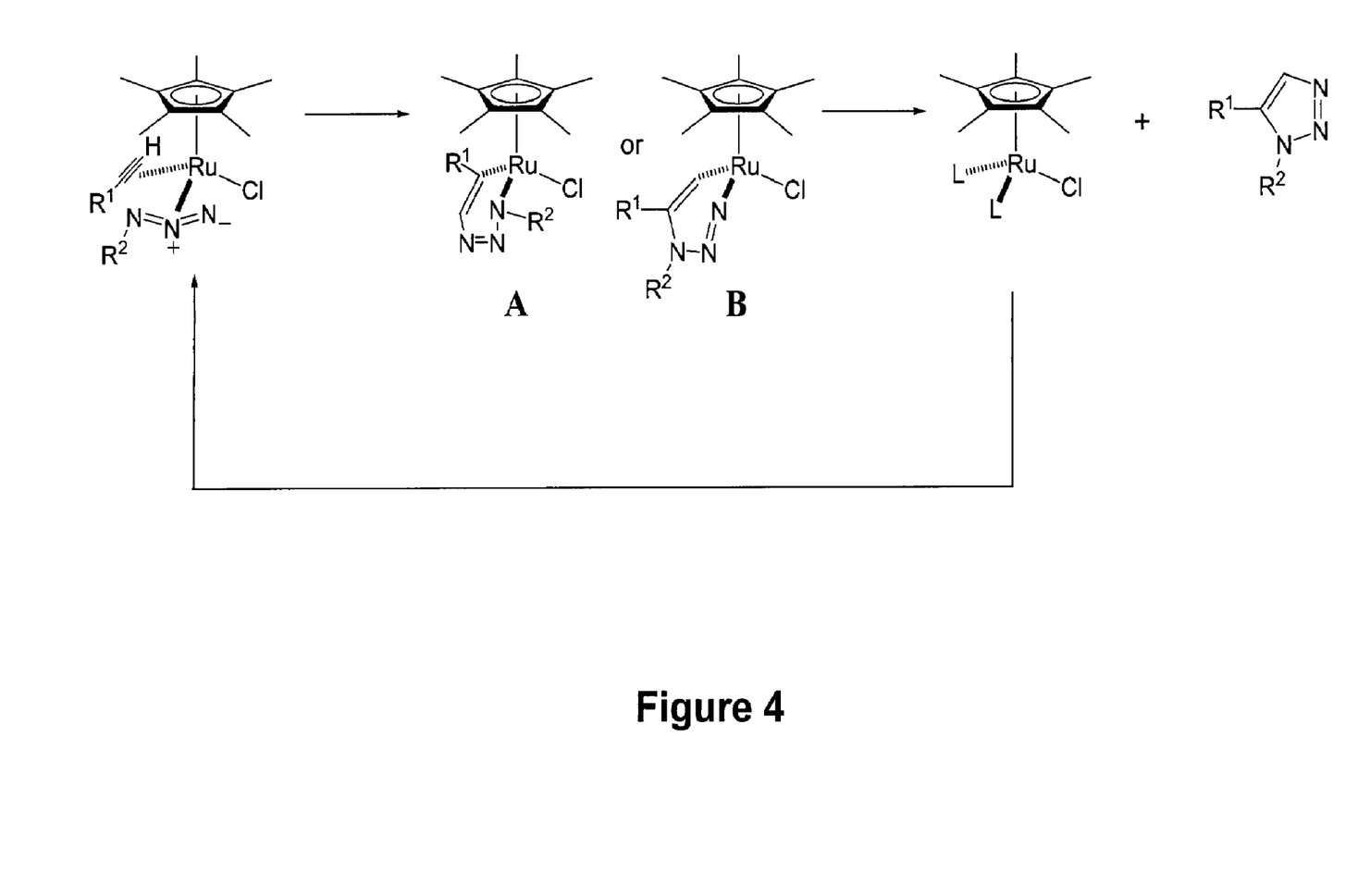
FIG. 4 illustrates the intermediates in the catalytic cycle.

FIG. 4 shows the proposed intermediates in the catalytic cycle. Ruthenium-catalyzed cyclotrimerization of alkynes is well known and, for the specific case of the Cp*RuCl(COD), has been shown to proceed via ruthenacyclopentadienes (Kirchner, K.; et al. *J. Am. Chem. Soc.* 2003, 125, 11721; Yamamoto, Y.; et al. *J. Am. Chem. Soc.* 2003, 125, 12413). Therefore, the newly-discovered Ru-catalyzed triazole annulations represent a simple, and early, shunt off the usual alkyne oligomerization sequence. That is, oxidative coupling of an alkyne and an azide on ruthenium may initially give a six-membered ruthenacycle (A is more likely than B), which then undergoes reductive elimination releasing the aromatic triazole product.

Figure 5:
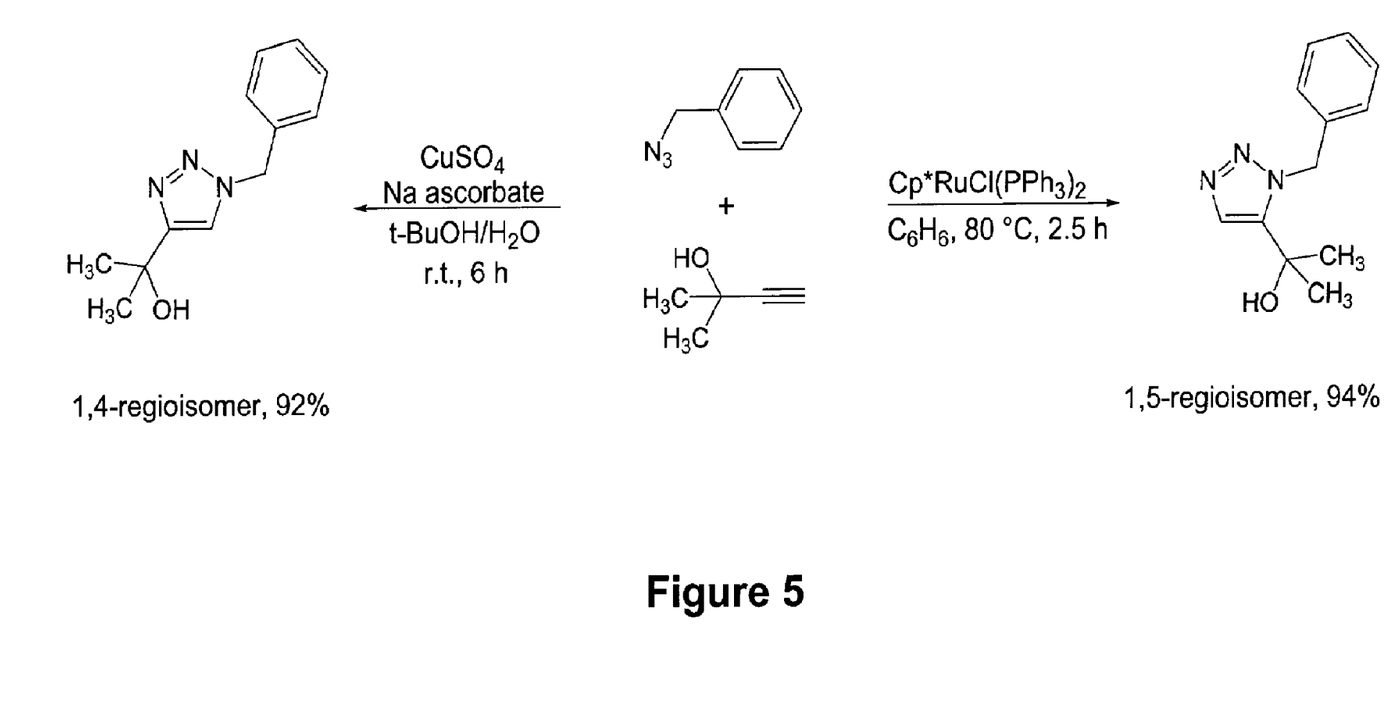
FIG. 5 illustrates the reactions required to produce the 1,4-regioisomer and the corresponding 1,5-regioisomer of 1,2,3-triazoles by the azide/alkyne cycloaddition.

FIG. 5 shows the reactions required to produce the 1,4-regioisomer and the corresponding 1,5-regioisomer of 1,2,3-triazoles by the azide/alkyne cycloaddition. The copper-catalyzed reaction gives the 1,4-regioisomers via a copper acetylide intermediate and the ruthenium-catalyzed variant gives the corresponding 1,5-regioisomer by a mechanism that likely bears resemblance to the cyclotrimerization of alkynes. Both reactions proceed in excellent yields with a variety of substrates.

What is claimed is:
1. A process for the formation of a 1,5-disubstituted 1,2,3-triazole or 1,4,5-trisubstituted 1,2,3-triazole, the process comprising the following steps:
   Step A: admixing a first compound having an acetylene group with a second compound having an azide group in a solvent for forming a reaction mixture wherein the azide group is bonded to an aliphatic carbon in the second compound; and then

Step B: contacting the reaction mixture of said Step A with a quantity of ruthenium catalyst sufficient for catalyzing the formation of the 1,5-disubstituted 1,2,3-triazole or the 1,4,5-trisubstituted 1,2,3-triazole, wherein the ruthenium catalyst comprises Ru(II) bearing a cyclopentadienylic ligand;

with the following provisos:
if the first compound is a terminal acetylene, then the product will be a 1,5-disubstituted 1,2,3-triazole; and
if the first compound is an internal acetylene, then the product will be a 1,4,5-trisubstituted 1,2,3-triazole.

2. The process according to claim 1 wherein the ruthenium catalyst is selected from the group consisting of Cp*RuCl (PPh$_3$)$_2$, [Cp*RuCl$_2$]$_2$, Cp*RuCl(NBD), and Cp*RuCl (COD), wherein Cp* is pentamethylcyclopentadienyl, NBD is norbornadienyl, and COD is cyclooctadienyl.

3. The process according to claim 1 wherein the solvent is selected from the group consisting of: benzene, toluene, tetrahydrofuran, and dioxane.

4. A method for preparing a 1,2,3-triazole comprising contacting an alkyne and an organic azide compound in a solvent with a ruthenium-based catalyst for a period of time sufficient to form a 1,2,3-triazole compound from the alkyne and the azide; wherein the ruthenium-based catalyst comprises Ru(II) bearing a cyclopentadienylic ligand.

5. The method of claim 4 wherein the cyclopentadienylic ligand is pentamethylcyclopentadienyl.

6. The method of claim 5 wherein the ruthenium-based catalyst is selected from the group consisting of bis-triphenylphosphino pentamethylcyclopentadienyl ruthenium (II) chloride, bis-[pentamethylcyclopentadienyl ruthenium (II) chloride], norbornadienyl pentamethylcyclopentadienyl ruthenium (II) chloride, and cyclooctadienyl pentamethylcyclopentadienyl ruthenium (II) chloride.

7. The method of claim 4 wherein the catalyst comprises cyclopentadienyl bis-triphenylphosphino ruthenium (II) chloride.

8. The method of claim 4 wherein the solvent is an aprotic solvent.

9. The method of claim 8 wherein the aprotic solvent comprises at least one solvent selected from the group consisting of benzene, toluene, tetrahydrofuxan, and dioxane.

10. The method of claim 4 wherein the alkyne and the organic azide are each present in the solvent at a concentration in the range of about 0.01 M to 1 M.

11. The method of claim 4 wherein the ruthenium-based catalyst is present in the solvent at a concentration in the range of about 1 to about 5 mol % based on the moles of alkyne or azide present.

12. The method of claim 4 wherein the solvent is maintained at a temperature in the range of about ambient room temperature to reflux temperature.

13. The method of claim 4 wherein the catalyst comprises a pentamethylcyclopentadienyl ruthenium (II) compound bearing a substituent selected from the group consisting of halide, alkylsulfonate, arylsulfonate, and cyanide.

14. The method of claim 4 wherein the alkyne is bonded to a radical selected from the group consisting of hydrogen, alkyl, alkenyl, aryl, heteroaryl, benzyl, propargyl, cycloalkyl, trialkylsilyl, alkyldiarylsilyl, dialkyiarylsilyl, trialkylstannyl, triarylsilyl, and cycloalkenyl.

15. The method of claim 4 wherein the organic azide is an aliphatic azide.

16. The method of claim 15 wherein the aliphatic azide is selected from the group consisting of a primary aliphatic azide, a tertiary azide, a benzylic azide and mixtures thereof.

17. A method for preparing a 1,5-disubstituted-1,2,3-triazole comprising contacting a terminal alkyne and an organic azide compound in a solvent with a ruthenium-based catalyst for a period of time sufficient to form a 1,5-disubstituted-1,2,3-triazole compound from the alkyne and the azide; wherein the ruthenium-based catalyst comprises Ru(II) bearing a pentamethylcyclopentadienyl ligand.

18. The method of claim 17 wherein the ruthenium-based catalyst is selected from the group consisting of bis-triphenylphosphino pentamethylcyclopentadienyl ruthenium (II) chloride, bis-[pentamethylcyclopentadienyl ruthenium (II) chloride], norbornadienyl pentamethylcyclopentadienyl ruthenium (II) chloride, and cyclooctadienyl pentamethylcyclopentadienyl ruthenium (II) chloride.

19. The method of claim 17 wherein the organic azide is a primary aliphatic azide, a tertiary azide or a benzylic azide.

20. The method of claim 17 wherein the solvent is an aprotic solvent.

21. The method of claim 17 wherein the alkyne and the organic azide are each present in the solvent at a concentration in the range of about 0.01 M to 1 M.

22. The method of claim 17 wherein the ruthenium-based catalyst is present in the solvent at a concentration in the range of about 1 to about 5 mol % based on the moles of alkyne or azide present.

23. A method for preparing a 1,4,5-trisubstituted-1,2,3-triazole comprising contacting an internal alkyne and an organic azide compound in a solvent with a ruthenium-based catalyst for a period of time sufficient to form a 1,4,5-trisubstituted-1,2,3-triazole compound from the alkyne and the azide; wherein the ruthenium-based catalyst comprises Ru(II) bearing a pentamethylcyclopentadienyl ligand.

24. The method of claim 23 wherein the ruthenium-based catalyst is selected from the group consisting of bis-triphenylphosphino pentamethylcyclopentadienyl ruthenium (II) chloride, bis-[pentamethylcyclopentadienyl ruthenium (II) chloride], norbornadienyl pentamethylcyclopentadienyl ruthenium (II) chloride, and cyclooctadienyl pentamethylcyclopentadienyl ruthenium (II) chloride.

25. The method of claim 23 wherein the organic azide is a primary aliphatic azide, a tertiary azide or a benzylic azide.

26. The method of claim 23 wherein the solvent is an aprotic solvent.

27. The method of claim 23 wherein the alkyne and the organic azide are each present in the solvent at a concentration in the range of about 0.01 M to 1 M.

28. The method of claim 23 wherein the ruthenium-based catalyst is present in the solvent at a concentration in the range of about 1 to about 5 mol % based on the moles of alkyne or azide present.

29. The method of claim 23 wherein the solvent is maintained at a temperature in the range of about ambient room temperature to reflux temperature.

30. The method according to claim 23 wherein the ruthenium catalyst is bis-triphenylphosphino pentamethylcyclopentadienyl ruthenium (II) chloride.

* * * * *